(12) United States Patent
Leinweber et al.

(10) Patent No.: US 8,067,651 B2
(45) Date of Patent: *Nov. 29, 2011

(54) 1-ALKYL-5-OXOPYRROLIDINE-3-CARBOXYLIC ESTERS WITH IMPROVED BIODEGRADABILITY

(75) Inventors: Dirk Leinweber, Kelkheim (DE); Alexander Roesch, Gimbsheim (DE); Michael Feustel, Köngernheim (DE)

(73) Assignee: Clariant Finance (BVI) Limited, Tortola (VG)

( * ) Notice: Subject to any disclaimer, the term of this patent is extended or adjusted under 35 U.S.C. 154(b) by 225 days.

This patent is subject to a terminal disclaimer.

(21) Appl. No.: 12/221,302

(22) Filed: Aug. 1, 2008

(65) Prior Publication Data

US 2009/0043146 A1 Feb. 12, 2009

(30) Foreign Application Priority Data

Aug. 6, 2007 (DE) .......................... 10 2007 037 017

(51) Int. Cl.
*C07D 207/28* (2006.01)
*C07D 207/00* (2006.01)

(52) U.S. Cl. ............................ 585/15; 585/950; 548/519

(58) Field of Classification Search .................. 548/519; 585/15

See application file for complete search history.

(56) References Cited

U.S. PATENT DOCUMENTS

| | | | |
|---|---|---|---|
| 3,224,975 A | 12/1965 | Hinkamp | |
| 4,127,493 A | 11/1978 | Elliott et al. | |
| 4,196,091 A * | 4/1980 | Schlicht | 508/297 |
| 4,774,255 A * | 9/1988 | Black et al. | 514/423 |
| 5,244,878 A | 9/1993 | Sugier et al. | |
| 5,880,252 A | 3/1999 | Kim et al. | |
| 6,093,862 A | 7/2000 | Sinquin et al. | |
| 6,566,309 B1 | 5/2003 | Klug et al. | |
| 6,894,007 B2 | 5/2005 | Klug et al. | |
| 7,615,102 B2 * | 11/2009 | Leinweber et al. | 95/153 |
| 7,893,009 B2 | 2/2011 | Leinweber et al. | |
| 2008/0177103 A1 | 7/2008 | Leinweber et al. | |
| 2008/0214865 A1 | 9/2008 | Leinweber et al. | |
| 2009/0042747 A1* | 2/2009 | Leinweber et al. | 507/202 |
| 2009/0054268 A1* | 2/2009 | Leinweber et al. | 507/90 |
| 2009/0124786 A1 | 5/2009 | Feustal et al. | |
| 2010/0213408 A1 | 8/2010 | Feustel et al. | |

FOREIGN PATENT DOCUMENTS

| | | |
|---|---|---|
| DE | 4333238 | 4/1995 |
| DE | 10259815 | 7/2004 |
| DE | 102005054037 | 5/2007 |
| DE | 102007037015 | 10/2008 |
| EP | 0069512 | 1/1983 |
| EP | 0896123 | 2/1999 |
| GB | 1323061 | 7/1973 |
| WO | WO93/25798 | 12/1993 |
| WO | WO2004/056885 | 7/2004 |
| WO | WO2006/084613 | 8/2006 |
| WO | WO2007/054225 | 5/2007 |
| WO | WO2007/054226 | 5/2007 |

OTHER PUBLICATIONS

English Lang. Abstract and Machine Trans. of DE10259815.
International Search Report for EP 08 01 3825, (Nov. 2008).
International Search Report for EP 08 01 3824, (Jan. 2009).

* cited by examiner

*Primary Examiner* — Ellen McAvoy
(74) *Attorney, Agent, or Firm* — Tod A. Waldrop

(57) ABSTRACT

The invention provides compounds of the formula 1

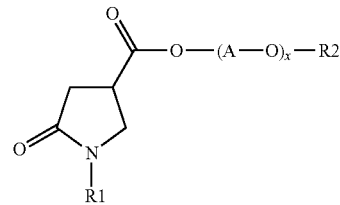

(1)

in which
A is a $C_2$- to $C_4$-alkylene group
x is from 1 to 100
R1 is $C_1$-$C_{30}$-alkyl, $C_2$-$C_{30}$-alkenyl, $C_7$-$C_{30}$-alkylaryl
R2 is an aliphatic, cycloaliphatic or aromatic radical which contains at least one structural unit of the formula 2

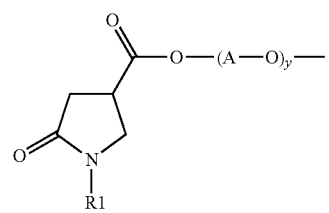

(2)

and
y is from 0 to 100,
with the proviso that y is from 1 to 100 when R2 is of the formula 2, and their use in amounts of from 0.01 to 2% by weight for preventing the formation of gas hydrates in aqueous phases which are in contact with a gaseous, liquid or solid organic phase.

9 Claims, No Drawings

1-ALKYL-5-OXOPYRROLIDINE-3-CARBOXYLIC ESTERS WITH IMPROVED BIODEGRADABILITY

The present invention is described in the German priority application No. 102007037017.4, filed Jun. 8, 2007, which is hereby incorporated by reference as is fully disclosed herein.

The present invention relates to 1-alkyl-5-oxopyrrolidine-3-carboxylic esters and their use as gas hydrate inhibitors.

Gas hydrates are crystalline inclusion compounds of gas molecules in water which form under certain temperature and pressure conditions (low temperature and high pressure). The water molecules form cage structures around the appropriate gas molecules. The lattice structure formed from the water molecules is thermodynamically unstable and is only stabilized by the incorporation of guest molecules. Depending on pressure and gas composition, these icelike compounds can exist even beyond the freezing point of water (up to above 25° C.).

In the mineral oil and natural gas industry, great significance attaches in particular to the gas hydrates which form from water and the natural gas constituents methane, ethane, propane, isobutane, n-butane, nitrogen, carbon dioxide and hydrogen sulfide. Especially in modern natural gas extraction, the existence of these gas hydrates constitutes a great problem, especially when wet gas or polyphasic mixtures of water, gas and alkane mixtures are subjected to low temperatures under high pressure. As a consequence of their insolubility and crystalline structure, the formation of gas hydrates leads here to the blockage of a wide variety of extraction equipment such as pipelines, valves or production equipment in which wet gas or polyphasic mixtures are transported over relatively long distances at relatively low temperatures, as occurs especially in colder regions of the earth or on the seabed.

Moreover, gas hydrate formation can also lead to problems in the course of the drilling operation to develop new gas or crude oil deposits at the appropriate pressure and temperature conditions by the formation of gas hydrates in the drilling fluids.

In order to prevent such problems, gas hydrate formation in gas pipelines, in the course of transport of polyphasic mixtures or in drilling fluids, can be suppressed by using relatively large amounts (more than 10% by weight, based on the weight of the aqueous phase) of lower alcohols such as methanol, glycol or diethylene glycol. The addition of these additives has the effect that the thermodynamic limit of gas hydrate formation is shifted to lower temperatures and higher pressures (thermodynamic inhibition). However, the addition of these thermodynamic inhibitors causes serious safety problems (flashpoint and toxicity of the alcohols), logistical problems (large storage tanks, recycling of these solvents) and accordingly high costs, especially in offshore extraction.

Attempts are therefore now being made to replace thermodynamic inhibitors by adding additives in amounts of <2% in temperature and pressure ranges in which gas hydrates can form. These additives either delay gas hydrate formation (kinetic inhibitors) or keep the gas hydrate agglomerates small and therefore pumpable, so that they can be transported through the pipeline (agglomerate inhibitors or anti-agglomerants). The inhibitors used either prevent nucleation and/or the growth of the gas hydrate particles, or modify the hydrate growth in such a way that relatively small hydrate particles result.

The gas hydrate inhibitors which have been described in the patent literature, in addition to the known thermodynamic inhibitors, are a multitude of monomeric and also polymeric substance classes which are kinetic inhibitors or antiagglomerants. Of particular significance in this context are polymers having a carbon backbone which contain both cyclic (pyrrolidone or caprolactam radicals) and acyclic amide structures in the side groups.

For instance, WO-94/12761 discloses a process for kinetically inhibiting gas hydrate formation by the use of polyvinyllactams having a molecular weight of $M_w$>40000 D, and WO-93/25798 discloses such a process using polymers and/or copolymers of vinylpyrrolidone having a molecular weight of $M_w$>5000 to 40000 D.

EP-A-0 896 123 discloses gas hydrate inhibitors which may comprise copolymers of alkoxylated methacrylic acid without alkyl end capping and cyclic N-vinyl compounds.

U.S. Pat. No. 5,244,878 describes a process for retarding the formation or reducing the tendency to form gas hydrates. To this end, polyols which are esterified with fatty acids or alkenylsuccinic anhydrides are used. The compounds prepared do not have any amino acid functions which can interact with clathrates (cage molecules).

The additives described have only limited efficacy as kinetic gas hydrate inhibitors and/or antiagglomerants, have to be used with coadditives, or are unobtainable in a sufficient amount or obtainable only at high cost.

In order to be able to use gas hydrate inhibitors even in the case of greater cooling than currently possible, i.e. further within the hydrate region, a further enhancement of action is required in comparison to the prior art hydrate inhibitors. In addition, improved products are desired with regard to their biodegradability.

It was thus an object of the present invention to find additives which both slow the formation of gas hydrates (kinetic inhibitors) and keep gas hydrate agglomerates small and pumpable (antiagglomerants), in order thus to ensure a broad spectrum of application with high potential action. Furthermore, they should be capable of replacing the currently used thermodynamic inhibitors (methanol and glycols), which cause considerable safety problems and logistical problems.

Since currently used inhibitors such as polyvinylpyrrolidone and polyvinylcaprolactam have only moderate biodegradability, the inventive compounds should additionally have improved biodegradability.

The prior art discloses 1-alkyl-5-oxopyrrolidine-3-carboxylic acid derivatives which are not used as gas hydrate inhibitors but rather in other fields.

For instance, GB-A-1 323 061 discloses N-substituted 5-oxopyrrolidine-3-carboxylic acids and their use in functional fluids, especially hydraulic fluids.

U.S. Pat. No. 3,224,975 discloses 1-alkyl-5-oxopyrrolidine-3-carboxylic acids which are used as anticorrosion additives in lubricants.

U.S. Pat. No. 4,127,493 discloses polyesters which are prepared by reacting N-substituted 5-oxopyrrolidine-3-carboxylic acids or esters with alkenylsuccinic acid or alkenylsuccinic anhydride, and their use as oil-soluble additives in lubricants.

EP-A-0 069 512 discloses N-substituted 5-oxopyrrolidine-3-carboxylic acid salts and their use as humectants.

As has now been found, surprisingly, both water-soluble and oil-soluble 1-alkyl-5-oxopyrrolidine-3-carboxylic esters are suitable as gas hydrate inhibitors. According to the structure, these esters may either delay the nucleation and growth of gas hydrates (kinetic gas hydrate inhibitors) or suppress the agglomeration of gas hydrates (antiagglomerants). In addition, the inventive compounds have significantly improved biodegradability.

The present invention provides compounds of the formula 1

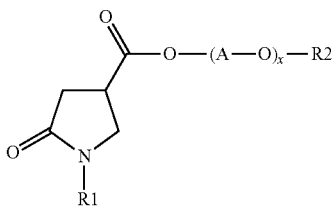

(1)

in which
A is a $C_2$- to $C_4$-alkylene group
x is from 1 to 100
R1 is $C_1$-$C_{30}$-alkyl, $C_2$-$C_{30}$-alkenyl, $C_7$-$C_{30}$-alkylaryl
R2 is an aliphatic, cycloaliphatic or aromatic radical which contains at least one structural unit of the formula 2

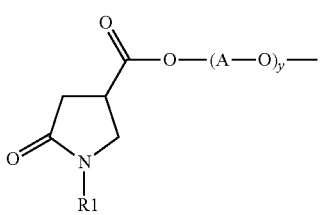

(2)

and
y is from 0 to 100,
with the proviso that y is from 1 to 100 when R2 is of the formula 2.

The invention further provides for the use of compounds of the formula 1 in amounts of from 0.01 to 2% by weight (based on the weight of the aqueous phase) for preventing the formation of gas hydrates in aqueous phases which are in contact with a gaseous, liquid or solid organic phase.

The invention further provides a process for inhibiting the formation of gas hydrates by adding at least one compound of the formula 1 in amounts of from 0.01 to 2% by weight (based on the weight of the aqueous phase) to an aqueous phase which is in contact with a gaseous, liquid or solid organic phase and in which gas hydrate formation is to be prevented.

R2 is an organic radical which contains one or more structural units of the formula 2. It can generally be represented by the formula 3

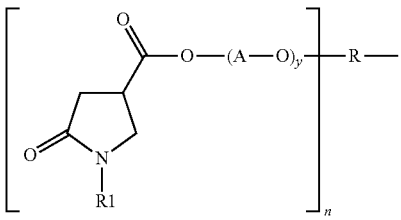

(3)

in which n is from 1 to 100 and R is a single bond or an aliphatic, cycloaliphatic or aromatic radical which may contain heteroatoms and arises through formal abstraction of the hydrogen atoms from a compound which bears at least (n+1) active hydrogen atoms which can be substituted by alkoxylation, and where R bears n structural units of the formula 2. R is preferably an organic radical which arises through formal abstraction of the hydrogen atoms from a compound which contains from two to six active hydrogen atoms. The active hydrogen atoms may stem, for example, from hydroxyl groups, amino groups or carboxyl groups which are bonded to alkyl, alkenyl, cycloalkyl, aryl, alkylaryl or polyoxyalkylene radicals.

In a preferred embodiment, R is an organic radical which arises through formal abstraction of the hydrogen atoms from a compound which contains two active hydrogen atoms and up to 100 carbon atoms. Accordingly, n is then 1.

R may comprise any further substituents, for example amino or amido substituents. R is more preferably an alkylene or polyalkylene oxide radical having from 1 to 30 carbon atoms.

In a further preferred embodiment, R is a radical which arises through formal abstraction of the hydrogen atoms of the OH groups of a polyol. Preferred polyols are ethylene glycol, propylene glycol, glycerol, diglycerol, triglycerol, tetraglycerol, polyglycerol, trimethylolpropane, pentaerythritol, dipentaerythritol, tripentaerythritol, sorbitol, sorbitan, diethylene glycol, triethylene glycol, propylene glycol, dipropylene glycol, tripropylene glycol and tris(hydroxymethyl)aminomethane. It is possible for all or only some of the hydrogen atoms of the polyols to be abstracted in the formation of R. It is preferred when 2, 3, 4, 5 or 6 hydrogen atoms of the OH groups of the polyol are abstracted, i.e. bear radicals of the formula 2.

R may also be a single bond. In this case, R2 is represented by the formula 2, such that the inventive compound corresponds to the formula 4:

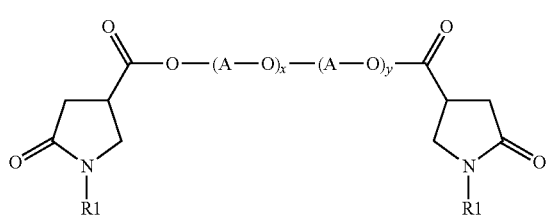

(4)

in this case, y is from 1 to 100.

R1 is preferably an aliphatic $C_1$-$C_{10}$ radical which may be branched or unbranched. R1 is more preferably an aliphatic $C_3$-$C_6$ radical, especially an aliphatic $C_4$ radical. According to the invention, it is also possible to use mixtures of 1-alkyl-5-oxopyrrolidine-3-carboxylic acids substituted by different R1 radicals to prepare the 1-alkyl-5-oxopyrrolidine-3-carboxylic esters.

A preferably represents ethylene radicals or mixtures of ethylene and propylene radicals.

In the alkoxy chain represented by (A-O)$_x$ or (A-O)$_y$, A is preferably an ethylene or propylene radical, especially an ethylene radical. x and y are preferably each independently from 1 to 80, in particular from 2 to 70, especially from 3 to 50. The alkoxy chain may be a block polymer chain which comprises alternating blocks of different alkoxy units, preferably ethoxy and propoxy units. It may also be a chain with a random sequence of the alkoxy units or a homopolymer.

In a preferred embodiment, $-(A-O)_x-$ or $-(A-O)_y-$ is an alkoxy chain of the formula

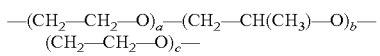

in which
a is from 1 to 100, preferably from 5 to 80,
b is from 0 to 100, preferably from 5 to 100,
c is from 1 to 100, preferably from 5 to 80.

In a further preferred embodiment, $-(A-O)_n-$ is an ethoxy radical having from 1 to 100 ethoxy units.

It is common to all embodiments that preferably at least 50 mol % of the (A-O) radicals are ethoxy radicals; in particular, from 60 to 100 mol % are ethoxy radicals.

Examples of inventive compounds are given in the following formulae 5 and 6:

(5)

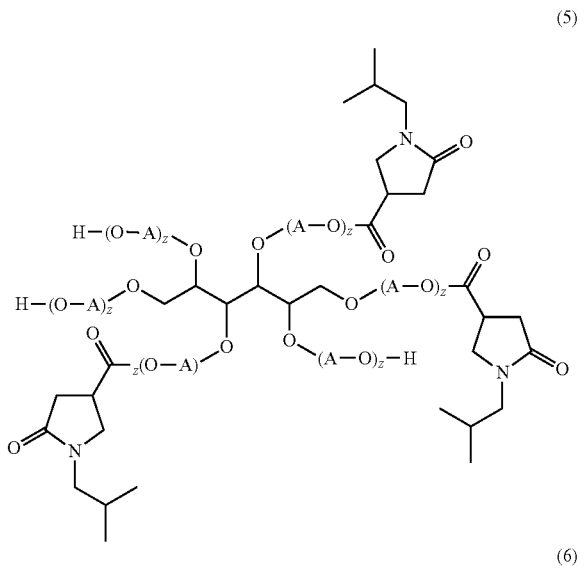

(6)

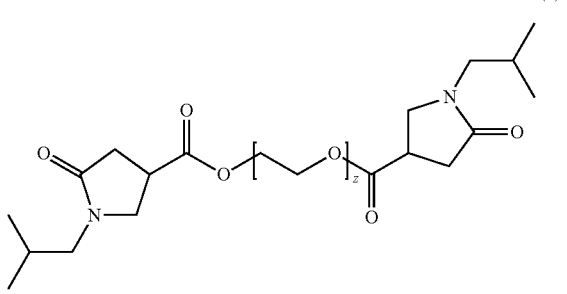

in which z may assume the values specified for x and y.
Formula 6 corresponds to the case when R is a single bond.

The inventive 1-alkyl-5-oxopyrrolidine-3-carboxylic esters can be prepared by esterifying 1-alkyl-5-oxopyrrolidine-3-carboxylic acid with at least one alcohol of the formula $HO-(A-O)_x-R-(O-A)_y-OH$. The preparation of the 1-alkyl-5-oxopyrrolidine-3-carboxylic acids is effected as described in detail in the prior art by reacting itaconic acid with primary amines and can be carried out as described in EP-A-0 069 512, U.S. Pat. Nos. 3,224,975 and 4,127,493.

The preparation of the inventive esters is known in the prior art and is effected by uncatalyzed or acid-catalyzed condensation of the carboxylic acid with the appropriate alcohol. The reaction temperature is generally between 100 and 300° C., preferably from 170 to 250° C. The molar ratio of OH groups in the alcohol to the 1-alkyl-5-oxopyrrolidine-3-carboxylic acid employed in the esterification is preferably between 1:0.3 and 1:1, especially between 1:0.5 and 1:1.

The reaction can be carried out at atmosphere pressure or reduced pressure. The catalyzing acids include, for example, HCl, $H_2SO_4$, sulfonic acids, $H_3PO_4$ or acidic ion exchangers, which are used in amounts from 0.1 to 5% by weight, based on the weight of the reaction mixture. The esterification takes generally from 3 to 30 hours.

The inventive 1-alkyl-5-oxopyrrolidine-3-carboxylic esters can be used alone or in combination with other known gas hydrate inhibitors. In general, an amount of the inventive 1-alkyl-5-oxopyrrolidine-3-carboxylic ester sufficient to obtain sufficient inhibition under the given pressure and temperature conditions will be added to the system which tends to form hydrates. The inventive 1-alkyl-5-oxopyrrolidine-3-carboxylic esters are preferably used in amounts between 0.02 and 2% by weight (based on the weight of the aqueous phase). When the inventive 1-alkyl-5-oxopyrrolidine-3-carboxylic esters are used in a mixture with other gas hydrate inhibitors, the concentration of the mixture is from 0.01 to 2 or from 0.02 to 1% by weight in the aqueous phase.

For use as gas hydrate inhibitors, the 1-alkyl-5-oxopyrrolidine-3-carboxylic esters are preferably dissolved in water or in water-miscible (preferably alcoholic) solvents, for example methanol, ethanol, propanol, butanol, ethylene glycol, 1,2-propylene glycol, 1,3-propylene glycol, glycerol, diethylene glycol, triethylene glycol, N-methylpyrrolidone, and oxyethylated monoalcohols such as butylglycol, isobutylglycol, butyldiglycol.

For use as gas hydrate inhibitors, oil-soluble 1-alkyl-5-oxopyrrolidine-3-carboxylic esters are preferably dissolved in relatively nonpolar solvents such as $C_3$-$C_8$ ketones, preferably diisobutyl ketone, methyl isobutyl ketone, cyclohexanone, or $C_5$-$C_{12}$-alcohols, for example 2-ethylhexanol.

EXAMPLES

Preparation of the
1-alkyl-5-oxopyrrolidine-3-carboxylic esters

Example 1

Preparation of triethylene glycol
di(1-methyl-5-oxopyrrolidine-3-carboxylate)

In a 500 ml four-neck flask with stirrer, thermometer, nitrogen purge and distillation system, 143 g of 1-methyl-5-oxopyrrolidine-3-carboxylic acid, 75 g of triethylene glycol and 1.0 g of p-toluenesulfonic acid were mixed and heated to 200° C. Within 8 h at 200° C., approx. 18 ml of water were distilled off. This afforded approx. 201 g of triethylene glycol di(1-methyl-5-oxopyrrolidine-3-carboxylate) with a hydrolysis number of 268 mg KOH/g.

Example 2

Preparation of (trimethylolpropane+9 EO)
tri(1-methyl-5-oxopyrrolidine-3-carboxylate)

In a 500 ml four-neck flask with stirrer, thermometer, nitrogen purge and distillation system, 143 g of 1-methyl-5-oxopyrrolidine-3-carboxylic acid, 177 g of trimethylolpropane+9 EO and 1.5 g of p-toluenesulfonic acid were mixed and heated to 200° C. Within 15 h at 200° C., approx. 18 ml of water were distilled off. This afforded approx. 304 g of (trimethylolpropane+9 EO) tri(1-methyl-5-oxopyrrolidine-3-carboxylate) with a hydrolysis number of 186 mg KOH/g.

Example 3

Preparation of (sorbitol+18 EO) tri(1-methyl-5-oxopyrrolidine-3-carboxylate)

In a 1000 ml four-neck flask with stirrer, thermometer, nitrogen purge and distillation system, 143 g of 1-methyl-5-oxopyrrolidine-3-carboxylic acid, 325 g of sorbitol+18 EO and 2.0 g of p-toluenesulfonic acid were mixed and heated to 200° C. Within 20 h at 200° C., approx. 18 ml of water were distilled off. This afforded approx. 451 g of (sorbitol+18 EO) tri(1-methyl-5-oxopyrrolidine-3-carboxylate) with a hydrolysis number of 125 mg KOH/g.

Example 4

Preparation of (sorbitol+30 EO) hexa(1-methyl-5-oxopyrrolidine-3-carboxylate)

In a 500 ml four-neck flask with stirrer, thermometer, nitrogen purge and distillation system, 143 g of 1-methyl-5-oxopyrrolidine-3-carboxylic acid, 250 g of sorbitol+30 EO and 2.0 g of p-toluenesulfonic acid were mixed and heated to 200° C. Within 20 h at 200° C., approx. 18 ml of water were distilled off. This afforded approx. 376 g of (sorbitol+30 EO) hexa(1-methyl-5-oxopyrrolidine-3-carboxylate) with a hydrolysis number of 149 mg KOH/g.

Example 5

Preparation of (decaglycerol+30 EO) poly(1-methyl-5-oxopyrrolidine-3-carboxylate)

In a 1000 ml four-neck flask with stirrer, thermometer, nitrogen purge and distillation system, 143 g of 1-methyl-5-oxopyrrolidine-3-carboxylic acid, 390 g of decaglycerol+30 EO and 2.5 g of p-toluenesulfonic acid were mixed and heated to 200° C. Within 30 h at 200° C., approx. 18 ml of water were distilled off. This afforded approx. 516 g of (decaglycerol+30 EO) poly(1-methyl-5-oxopyrrolidine-3-carboxylate) with a hydrolysis number of 104 mg KOH/g.

Example 6

Preparation of (polypropylene glycol 400+10 EO) di(1-methyl-5-oxopyrrolidine-3-carboxylate)

In a 1000 ml four-neck flask with stirrer, thermometer, nitrogen purge and distillation system, 143 g of 1-methyl-5-oxopyrrolidine-3-carboxylic acid, 420 g of polypropylene glycol 400+10 EO and 2.5 g of p-toluenesulfonic acid were mixed and heated to 200° C. Within 18 h at 200° C., approx. 18 ml of water were distilled off. This afforded approx. 546 g of (polypropylene glycol 400+10 EO) di(1-methyl-5-oxopyrrolidine-3-carboxylate) with a hydrolysis number of 103 mg KOH/g.

Example 7

Preparation of (polypropylene glycol 600) di(1-methyl-5-oxopyrrolidine-3-carboxylate)

In a 1000 ml four-neck flask with stirrer, thermometer, nitrogen purge and distillation system, 143 g of 1-methyl-5-oxopyrrolidine-3-carboxylic acid, 300 g of polypropylene glycol 600 and 2.0 g of p-toluenesulfonic acid were mixed and heated to 200° C. Within 20 h at 200° C., approx. 18 ml of water were distilled off. This afforded approx. 426 g of (polypropylene glycol 600) di(1-methyl-5-oxopyrrolidine-3-carboxylate) with a hydrolysis number of 132 mg KOH/g.

Example 8

Preparation of triethylene glycol di(1-isobutyl-5-oxopyrrolidine-3-carboxylate)

In a 500 ml four-neck flask with stirrer, thermometer, nitrogen purge and distillation system, 185 g of 1-isobutyl-5-oxopyrrolidine-3-carboxylic acid, 75 g of triethylene glycol and 1.5 g of p-toluenesulfonic acid were mixed and heated to 200° C. Within 8 h at 200° C., approx. 18 ml of water were distilled off. This afforded approx. 243 g of triethylene glycol di(1-isobutyl-5-oxopyrrolidine-3-carboxylate) with a hydrolysis number of 231 mg KOH/g.

Example 9

Preparation of (trimethylolpropane+9 EO) tri(1-isobutyl-5-oxopyrrolidine-3-carboxylate)

In a 500 ml four-neck flask with stirrer, thermometer, nitrogen purge and distillation system, 185 g of 1-isobutyl-5-oxopyrrolidine-3-carboxylic acid, 177 g of trimethylolpropane+9 EO and 1.5 g of p-toluenesulfonic acid were mixed and heated to 200° C. Within 15 h at 200° C., approx. 18 ml of water were distilled off. This afforded approx. 346 g of (trimethylolpropane+9 EO) tri(1-isobutyl-5-oxopyrrolidine-3-carboxylate) with a hydrolysis number of 163 mg KOH/g.

Example 10

Preparation of (sorbitol+18 EO) tri(1-isobutyl-5-oxopyrrolidine-3-carboxylate)

In a 1000 ml four-neck flask with stirrer, thermometer, nitrogen purge and distillation system, 185 g of 1-isobutyl-5-oxopyrrolidine-3-carboxylic acid, 325 g of sorbitol+18 EO and 2.5 g of p-toluenesulfonic acid were mixed and heated to 200° C. Within 20 h at 200° C., approx. 18 ml of water were distilled off. This afforded approx. 492 g of (sorbitol+18 EO) tri(1-isobutyl-5-oxopyrrolidine-3-carboxylate) with a hydrolysis number of 114 mg KOH/g.

Example 11

Preparation of (sorbitol+30 EO) hexa(1-isobutyl-5-oxopyrrolidine-3-carboxylate)

In a 1000 ml four-neck flask with stirrer, thermometer, nitrogen purge and distillation system, 185 g of 1-isobutyl-5-oxopyrrolidine-3-carboxylic acid, 250 g of sorbitol+30 EO and 2.0 g of p-toluenesulfonic acid were mixed and heated to 200° C. Within 20 h at 200° C., approx. 18 ml of water were distilled off. This afforded approx. 419 g of (sorbitol+30 EO) hexa(1-isobutyl-5-oxopyrrolidine-3-carboxylate) with a hydrolysis number of 135 mg KOH/g.

Example 12

Preparation of (decaglycerol+30 EO) poly(1-isobutyl-5-oxopyrrolidine-3-carboxylate)

In a 1000 ml four-neck flask with stirrer, thermometer, nitrogen purge and distillation system, 185 g of 1-isobutyl-5- oxopyrrolidine-3-carboxylic acid, 390 g of decaglycerol+30 EO and 2.5 g of p-toluenesulfonic acid were mixed and heated to 200° C. Within 30 h at 200° C., approx. 18 ml of water were distilled off. This afforded approx. 556 g of (decaglycerol+30 EO) poly(1-isobutyl-5-oxopyrrolidine-3-carboxylate) with a hydrolysis number of 100 mg KOH/g.

Example 13

Preparation of (polypropylene glycol 400+10 EO) di(1-isobutyl-5-oxopyrrolidine-3-carboxylate)

In a 1000 ml four-neck flask with stirrer, thermometer, nitrogen purge and distillation system, 185 g of 1-isobutyl-5-oxopyrrolidine-3-carboxylic acid, 420 g of polypropylene glycol 400+10 EO and 2.5 g of p-toluenesulfonic acid were mixed and heated to 200° C. Within 18 h at 200° C., approx. 18 ml of water were distilled off. This afforded approx. 586 g of (polypropylene glycol 400+10 EO) di(1-isobutyl-5-oxopyrrolidine-3-carboxylate) with a hydrolysis number of 95 mg KOH/g.

Example 14

Preparation of (polypropylene glycol 600) di(1-isobutyl-5-oxopyrrolidine-3-carboxylate)

In a 1000 ml four-neck flask with stirrer, thermometer, nitrogen purge and distillation system, 185 g of 1-isobutyl-5-oxopyrrolidine-3-carboxylic acid, 300 g of polypropylene glycol 600 and 2.0 g of p-toluenesulfonic acid were mixed and heated to 200° C. Within 20 h at 200° C., approx. 18 ml of water were distilled off. This afforded approx. 467 g of (polypropylene glycol 600) di(1-isobutyl-5-oxopyrrolidine-3-carboxylate) with a hydrolysis number of 120 mg KOH/g.

Example 15

Preparation of triethylene glycol di(1-oleyl-5-oxopyrrolidine-3-carboxylate)

In a 1000 ml four-neck flask with stirrer, thermometer, nitrogen purge and distillation system, 380 g of 1-oleyl-5-oxopyrrolidine-3-carboxylic acid, 75 g of triethylene glycol and 2.0 g of p-toluenesulfonic acid were mixed and heated to 200° C. Within 8 h at 200° C., approx. 18 ml of water were distilled off. This afforded approx. 438 g of triethylene glycol di(1-oleyl-5-oxopyrrolidine-3-carboxylate) with a hydrolysis number of 129 mg KOH/g.

Example 16

Preparation of (trimethylolpropane+9 EO) tri(1-oleyl-5-oxopyrrolidine-3-carboxylate)

In a 1000 ml four-neck flask with stirrer, thermometer, nitrogen purge and distillation system, 380 g of 1-oleyl-5-oxopyrrolidine-3-carboxylic acid, 177 g of trimethylolpropane+9 EO and 2.5 g of p-toluenesulfonic acid were mixed and heated to 200° C. Within 15 h at 200° C., approx. 18 ml of water were distilled off. This afforded approx. 540 g of (trimethylolpropane+9 EO) tri(1-oleyl-5-oxopyrrolidine-3-carboxylate) with a hydrolysis number of 105 mg KOH/g.

Example 17

Preparation of (sorbitol+18 EO) tri(1-oleyl-5-oxopyrrolidine-3-carboxylate)

In a 1000 ml four-neck flask with stirrer, thermometer, nitrogen purge and distillation system, 380 g of 1-oleyl-5-oxopyrrolidine-3-carboxylic acid, 325 g of sorbitol+18 EO and 3.0 g of p-toluenesulfonic acid were mixed and heated to 200° C. Within 20 h at 200° C., approx. 18 ml of water were distilled off. This afforded approx. 686 g of (sorbitol+18 EO) tri(1-oleyl-5-oxopyrrolidine-3-carboxylate) with a hydrolysis number of 82 mg KOH/g.

Example 18

Preparation of (sorbitol+30 EO) hexa(1-oleyl-5-oxopyrrolidine-3-carboxylate)

In a 1000 ml four-neck flask with stirrer, thermometer, nitrogen purge and distillation system, 380 g of 1-oleyl-5-oxopyrrolidine-3-carboxylic acid, 250 g of sorbitol+30 EO and 3.0 g of p-toluenesulfonic acid were mixed and heated to 200° C. Within 20 h at 200° C., approx. 18 ml of water were distilled off. This afforded approx. 613 g of (sorbitol+30 EO) hexa(1-oleyl-5-oxopyrrolidine-3-carboxylate) with a hydrolysis number of 92 mg KOH/g.

Example 19

Preparation of (decaglycerol+30 EO) poly(1-oleyl-5-oxopyrrolidine-3-carboxylate)

In a 1000 ml four-neck flask with stirrer, thermometer, nitrogen purge and distillation system, 380 g of 1-oleyl-5-oxopyrrolidine-3-carboxylic acid, 390 g of decaglycerol+30 EO and 3.0 g of p-toluenesulfonic acid were mixed and heated to 200° C. Within 30 h at 200° C., approx. 18 ml of water were distilled off. This afforded approx. 750 g of (decaglycerol+30 EO) poly(1-oleyl-5-oxopyrrolidine-3-carboxylate) with a hydrolysis number of 72 mg KOH/g.

Example 20

Preparation of (polypropylene glycol 400+10 EO) di(1-oleyl-5-oxopyrrolidine-3-carboxylate)

In a 1000 ml four-neck flask with stirrer, thermometer, nitrogen purge and distillation system, 380 g of 1-oleyl-5-oxopyrrolidine-3-carboxylic acid, 420 g of polypropylene glycol 400+10 EO and 3.0 g of p-toluenesulfonic acid were mixed and heated to 200° C. Within 18 h at 200° C., approx. 18 ml of water were distilled off. This afforded approx. 780 g of (polypropylene glycol 400+10 EO) di(1-oleyl-5-oxopyrrolidine-3-carboxylate) with a hydrolysis number of 72 mg KOH/g.

Example 21

Preparation of (polypropylene glycol 600) di(1-oleyl-5-oxopyrrolidine-3-carboxylate)

In a 1000 ml four-neck flask with stirrer, thermometer, nitrogen purge and distillation system, 380 g of 1-oleyl-5-oxopyrrolidine-3-carboxylic acid, 300 g of polypropylene glycol 600 and 3.0 g of p-toluenesulfonic acid were mixed and heated to 200° C. Within 20 h at 200° C., approx. 18 ml of water were distilled off. This afforded approx. 660 g of (polypropylene glycol 600) di(1-oleyl-5-oxopyrrolidine-3-carboxylate) with a hydrolysis number of 85 mg KOH/g.

Efficacy of the polymers as gas hydrate inhibitors

To study the inhibiting action of the polyesters, a stirred steel autoclave with temperature control, pressure and torque sensor of capacity 450 ml was used. For studies of kinetic inhibition, the autoclave was filled with distilled water and gas in a volume ratio of 20:80; for studies of agglomerate inhibition, condensate was additionally added. Subsequently, 50 bar of natural gas were injected.

Proceeding from a starting temperature of 20° C., the autoclave was cooled to 4° C. within 3 h, then stirred at 4° C. for 18 h and heated back to 20° C. within 2 h. At first, a pressure decrease corresponding to the thermal compression of the gas is observed. When the formation of gas hydrate nuclei occurs during the cooling time, the pressure measured falls, and a rise in the torque measured and a slight increase in the temperature are observed. Without inhibitor, further growth and increasing agglomeration of the hydrate nuclei lead rapidly to a further rise in the torque. When the mixture is heated, the gas hydrates decompose, so that the starting state of the experimental series is attained.

The measure used for the inhibiting action of the polymer is the time from the attainment of the minimum temperature of 4° C. until the first gas absorption ($T_{ind}$) or the time until the torque rises ($T_{agg}$). Long induction times or agglomeration times indicate an effect as a kinetic inhibitor. The torque measured in the autoclave serves, in contrast, as a parameter for the agglomeration of the hydrate crystals. In the case of a good antiagglomerant, the torque which builds up after gas hydrates have formed is significantly reduced compared to the blank value. In the ideal case, snowlike, fine hydrate crystals form in the condensate phase, do not agglomerate and thus do not lead to blockage of the installations serving for gas transport and for gas extraction.

Test Results

Composition of the natural gas used:

methane 84.8%, ethane 9.2%, propane 2.6%, butane 0.9%, carbon dioxide 1.6%, nitrogen 0.9%.

The comparative substance used was a commercially available gas hydrate inhibitor based on polyvinylpyrrolidone. The dosage in all tests was 5000 ppm based on the water phase.

In order to test the action as agglomerate inhibitors, the test autoclave used above was initially charged with water and white spirit (20% of the volume in a ratio of 1:2) and, based on the water phase, 5000 ppm of the particular additive were added.

At an autoclave pressure of 50 bar and a stirrer speed of 500 rpm, the temperature of initially 20° C. was cooled to 4° C. within 3 hours, then the autoclave was stirred at 2° C. for 18 hours and warmed up again. In the course of this, the agglomeration time until the occurrence of gas hydrate agglomerates and the torque which occurred on the stirrer at that time were measured, the latter being a measure of the agglomeration of the gas hydrates.

The comparative substance employed was a commercially available antiagglomerant (quaternary ammonium salt).

| 1-alkyl-5-oxopyrrolidine-3-carboxylic ester from example | $T_{agg}$ (h) | $M_{max}$ (Ncm) |
|---|---|---|
| Blank value | 0.1 | 15.9 |
| 6 | 7.5 | 0.9 |
| 7 | 6.9 | 1.0 |
| 13 | 8.9 | 1.0 |
| 14 | 10.5 | 1.0 |
| 15 | 4.1 | 1.6 |
| 16 | 4.8 | 1.8 |
| 17 | 4.5 | 1.5 |
| 18 | 4.5 | 2.0 |
| 19 | 4.6 | 2.1 |
| 20 | 4.9 | 1.6 |
| 21 | 4.0 | 1.7 |
| Comparative | 2.6 | 4.1 |

As can be seen from these examples, the torques measured are greatly reduced compared to the blank value in spite of gas hydrate formation. This supports a significant agglomerate-inhibiting action of the inventive products. In addition, the products also have significant action as kinetic inhibitors under the test conditions. All examples show a significantly better performance than the commercially available antiagglomerant (comparative=state of the art).

The significantly improved biodegradability (to OECD 306) of the inventive compounds compared to the state of the art (commercially available polyvinylpyrrolidone) is shown hereinafter.

| 1-alkyl-5-oxopyrrolidine-3-carboxylic ester from example | $T_{ind}$ (h) | $T_{agg}$ (h) |
|---|---|---|
| Blank value | 0 | 0 |
| 1 | 12.4 | 12.5 |
| 2 | 13.1 | 13.3 |
| 3 | 14.1 | 14.1 |
| 4 | 14.3 | 14.5 |
| 5 | 12.8 | 13.0 |
| 6 | 9.9 | 10.1 |
| 8 | 20.9 | 22.1 |
| 9 | 22.0 | 23.4 |
| 10 | 24.0 | 24.9 |
| 11 | 25.7 | 26.5 |
| 12 | 23.3 | 23.5 |
| 13 | 15.1 | 15.8 |
| Comparative | 3.5 | 3.6 |

As can be seen from the above test results, the inventive 1-alkyl-5-oxopyrrolidine-3-carboxylic esters act as kinetic gas hydrate inhibitors and show a clear improvement over the prior art.

| 1-alkyl-5-oxopyrrolidine-3-carboxylic ester from example | Biodegradability 28 days (OECD 306) |
|---|---|
| polyvinylpyrrolidone | 5 |
| 1 | 65 |
| 2 | 61 |
| 3 | 70 |
| 4 | 72 |
| 5 | 45 |
| 6 | 30 |
| 7 | 25 |
| 8 | 69 |
| 9 | 66 |
| 10 | 73 |
| 11 | 73 |
| 12 | 38 |
| 13 | 33 |
| 14 | 25 |
| 15 | 42 |
| 16 | 40 |
| 17 | 36 |
| 18 | 35 |

-continued

| 1-alkyl-5-oxopyrrolidine-3-carboxylic ester from example | Biodegradability 28 days (OECD 306) |
|---|---|
| 19 | 33 |
| 20 | 23 |
| 21 | 24 |

The invention claimed is:

1. A compound of the formula 1

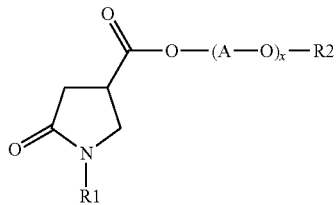
(1)

wherein

A is a $C_2$- to $C_4$-alkylene group x is from 1 to 100

R1 is $C_1$-$C_{30}$-alkyl, $C_2$-$C_{30}$-alkenyl, $C_7$-$C_{30}$-alkylaryl

R2 is an aliphatic, cycloaliphatic or aromatic radical containing at least one structural unit of the formula 2

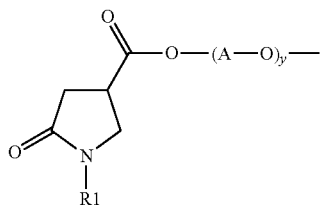
(2)

and y is from 0 to 100, with the proviso that y is from 1 to 100 when R2 is of the formula 2.

2. A compound as claimed in claim 1, wherein x and y are each independently from 2 to 80.

3. A compound as claimed in claim 1, wherein R2 is an organic radical of the formula 3

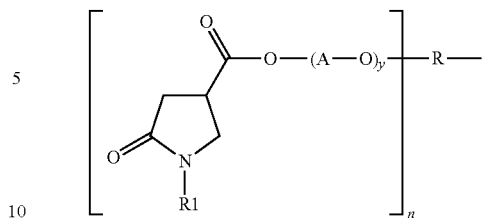
(3)

in which n is from 1 to 100 and R is a single bond or an aliphatic, cycloaliphatic or aromatic radical, optionally containing heteroatoms and arises through formal abstraction of the hydrogen atoms from a compound having at least (n+1) active hydrogen atoms which can be substituted by alkoxylation.

4. A compound as claimed in claim 3, in which R is an organic radical which arises through formal abstraction of the hydrogen atoms from a compound which contains from two to six active hydrogen atoms.

5. A compound as claimed in claim 3 wherein R2 is derived from ethylene glycol, propylene glycol, glycerol, diglycerol, triglycerol, tetraglycerol, polyglycerol, trimethylolpropane, pentaerythritol, dipentaerythritol, tripentaerythritol, sorbitol, sorbitan, diethylene glycol, triethylene glycol, propylene glycol, dipropylene glycol, tripropylene glycol or tris(hydroxymethyl)aminomethane.

6. A compound as claimed in claim 1, having the formula 4

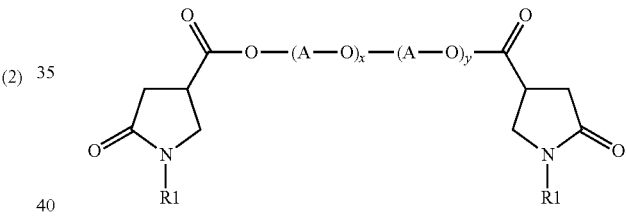
(4)

which wherein y is from 1 to 100.

7. A compound as claimed in claim 1, wherein R1 is an aliphatic $C_1$-$C_{10}$ radical.

8. A compound as claimed in claim 1, wherein A represents ethylene radicals, propylene radicals or mixtures of ethylene and propylene radicals.

9. A process for preventing the formation of gas hydrates in an aqueous phase, wherein the aqueous phase is in contact with a gaseous, liquid or solid organic phase comprising the step of contacting a compound as claimed in claim 1 in an amount of from 0.01 to 2% by weight, based on the weight of the aqueous phase.

* * * * *